US00PP37591P2

(12) United States Plant Patent
Byrne et al.

(10) Patent No.: US PP37,591 P2
(45) Date of Patent: Aug. 18, 2026

(54) PEACH TREE NAMED 'TRH3E88LW'

(50) Latin Name: *Prunus persica*
Varietal Denomination: TRH3E88LW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,368

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.

*Primary Examiner* — Karen M Redden
(74) *Attorney, Agent, or Firm* — Dentons US LLP

(57) ABSTRACT

Disclosed is a new variety of *Prunus persica* named 'TRH3E88LW'. This new variety, which requires approximately 450 chilling units of dormancy, is considered to be a peach tree of early mid-season maturity, which produces white-fleshed. subacid fruit that are firm with a 70-90% dark reddish pink blush over a greenish-white ground color and suitable for the fresh fruit market.

5 Drawing Sheets

Latin name of the genus and species of the plant claimed: *Prunus persica.*

Variety denomination: 'TRH3E88LW'.

CROSS-REFERENCE TO RELATED APPLICATIONS

Peach trees developed under the same breeding program as 'TRH3E88LW' include the co- pending applications listed below.

| U.S. application No. Ser. No. | Title |
|---|---|
| U.S. 19/336,141 | PEACH TREE NAMED 'TX3C490L WP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,370 | PEACH TREE NAMED 'TX2B449LW' |
| U.S. 19/336,372 | PEACH TREE NAMED 'TX2C465CW' |
| U.S. 19/336,375 | PEACH TREE NAMED 'TX2C465CW' |
| U.S. 19/336,377 | PEACH TREE NAMED 'TRH3C111' |
| U.S. 19/336,380 | PEACH TREE NAMED 'TRH2C108W' |

-continued

| U.S. application No. Ser. No. | Title |
|---|---|
| U.S. 19/336,383 | PEACH TREE NAMED 'TRH2E116L' |
| U.S. 19/336,385 | PEACH TREE NAMED 'TRH2B 102LW' |

BACKGROUND OF THE INVENTION

This invention relates to a peach tree and, more specifically, to a peach tree referred to as a variety of *Prunus persica* named 'TRH3E88LW', which requires approximately 450 chilling units of dormancy, produces a firm semi-freestone, white-fleshed, subacid peach that matures early mid-season. The present peach tree was the result of an ongoing Stone Fruit Breeding Program in College Station, Brazos County, Texas. To this end, controlled crosses were made each year to produce seedling populations from which improved progenies are evaluated and selected. 'TRH3E88LW' was derived from a population created by crossing the medium chill, yellow-fleshed, acid-sweet nectarine selection 'TXC95128N' (not patented) with the high chill white-fleshed, subacid, non-melting peach selection, 'BY96P3606' (not patented). 'TXC95128N' was a selection from an open pollinated population derived from the selection, 'FLA82-23N' (not patented).

The parents of 'FLA82-23N' were 'Lara' (not patented) and 'Maravilha' (not patented; Sherman, W. B., J. Rodriguez-Alcazar, and B. L. Topp. 1992. Peaches and nectarines developed but not introduced by the University of Florida. Fruit Varieties Journal 46:124-127). The USDA selection 'BY96P3606' was a selection from the cross between the USDA selection 'P34-157' (not patented) and the Chinese peach 'Yan Hong' (not patented; Wang, L. 2012. Peach genetic resource in China. Zhengzhou Fruit Research Institute, Zhengzhou, China). 'P34-157' is a cross between 'Flavorcrest' (not patented) and the New Jersey selection 'C2-22-17' (not patented). The parentage of 'C2-22-17' is 'NJ230' (not patented) and 'NJN54' (not patented). 'NJ230' is a cross between 'Jerseyland' (not patented) and 'Prariedawn' (not patented). 'NJN54' was selected from a population derived by collecting open pollinated seed of the selection '5107397' (not patented) which in turn has the parentage of the selection '53739' (not patented) and 'NJN17' (not patented). The selection '53739' is a cross between the peach 'Candoka' (U.S. Plant Pat. No. 51) and the nectarine 'Flaminggold' (not patented). 'NJN17' (not patented) is from a population created by collecting open pollinated seed from 'NJN5' (not patented) which is a cross between the peach 'Garden State' (not patented) and the selection 'NJ25032' (not patented). This is a selection from seed collected from 'Tennessee Natural' (not patented) (Okie, 1998). Resulting seed from the 'TXC95128N' x 'BY96P3606' hybrid were planted in 2010 in an experimental plot in Floresville, TX. 'TRH3E88LW' was marked for subsequent observation in 2012 and noted as having exceptional characteristics.

'TRH3E88LW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Somerville (2016-2023) and Fairfield (2014-2022), Texas. This evaluation clearly demonstrated that the re-propagated trees were true to the characteristics of the original seedling in all observable aspects.

SUMMARY OF THE INVENTION

The 'TRH3E88LW' peach is characterized by producing semi freestone, white-fleshed, subacid fruit that ripens in the early mid-season and produces a firm fruit with a dark reddish pink blush over a greenish white ground color. In this regard, the present variety of medium chill peach tree bears fruit that are ripe for commercial harvesting and shipment in early June, when the fruit is grown in the medium chill zone of Texas. 'TRH3E88LW' blooms with its female parent 'TXC95128N' (not patented), and 3-4 weeks before its pollen parent 'BY96P3606' (not patented). It ripens 10-14 days after its female parent and about one week before its pollen parent. 'TRH3E88LW' differs from its yellow-fleshed, acid, nectarine female parent as it is white-fleshed, subacid peach and from its high-chill, white-fleshed, subacid peach pollen parent as it requires ~300 chill hours less to fruit. This new subacid, white-fleshed, semi freestone peach exhibits potential to be commercialized in regions that have chilling requirements that are moderately low.

'TRH3E88LW' as compared to two commercial subacid, white-fleshed peaches 'White Delight One' (not patented, USPP App. Pub. No. 2016/0205833 P1, abandoned) and 'White Delight Two' (not patented, US App. Pub. No. 2016/0205832 P1, abandoned) has showy rather than non showy flowers, reniform rather than globose glands, requires 100 less chilling hours to fruit properly and blooms about one week earlier than 'White Delight One' and 'White Delight Two'. In addition 'White Delight One' ripens about one month earlier than 'TRH3E88LW'.

BRIEF DESCRIPTION OF THE DRAWINGS

This new variety of peach tree is illustrated by the accompanying photographs of 3-year to 5-year old plants grown in Somerville, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
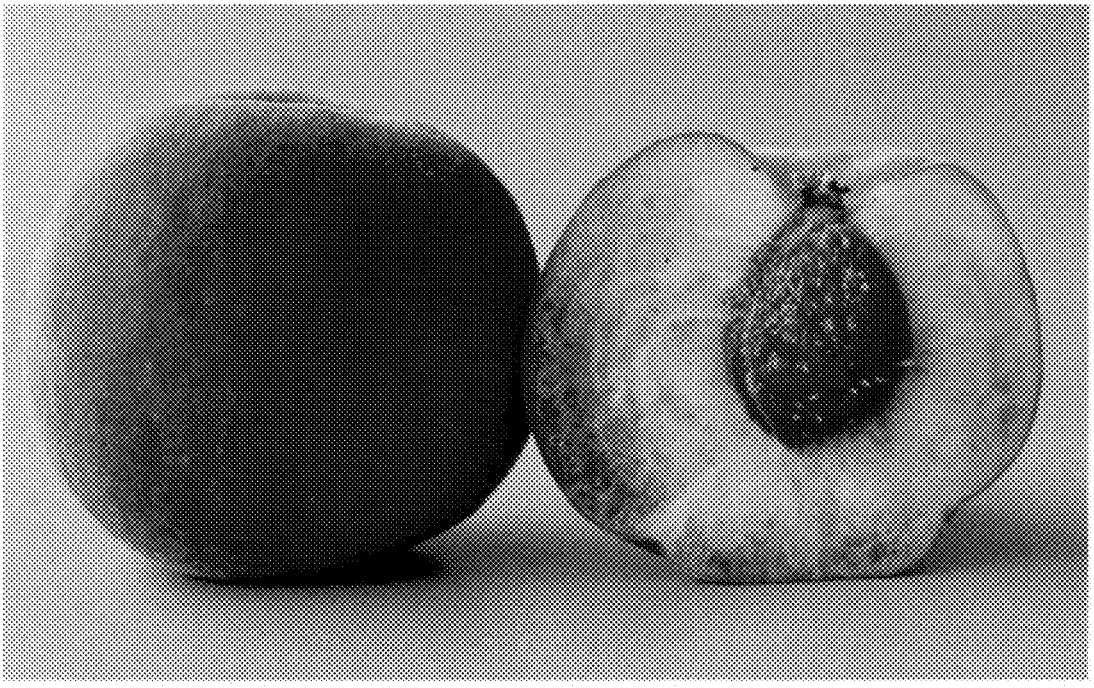
FIG. 1. Fruit of 'TRH3E88LW' produced in Somerville, Texas showing external and internal coloration.
Figure 2:
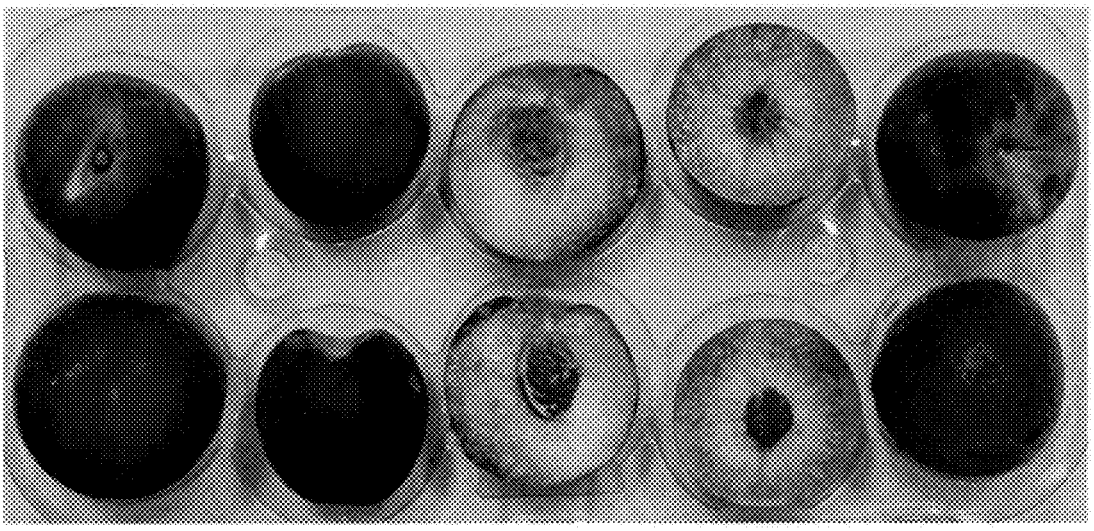
FIG. 2. 'TRH3E88LW' fruit produced in Somerville, Texas showing shape and external coloration.
Figure 3:
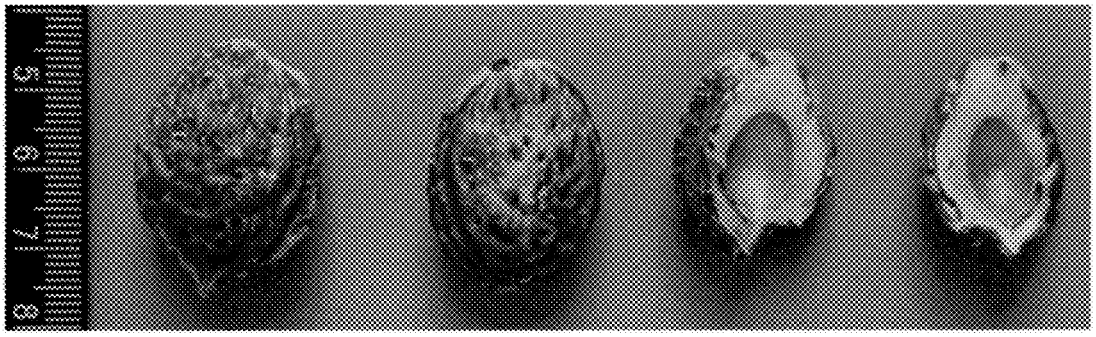
FIG. 3. Photograph of the endocarps of 'TRH3E88LW' peach. The ruler is in centimeters.
Figure 4:
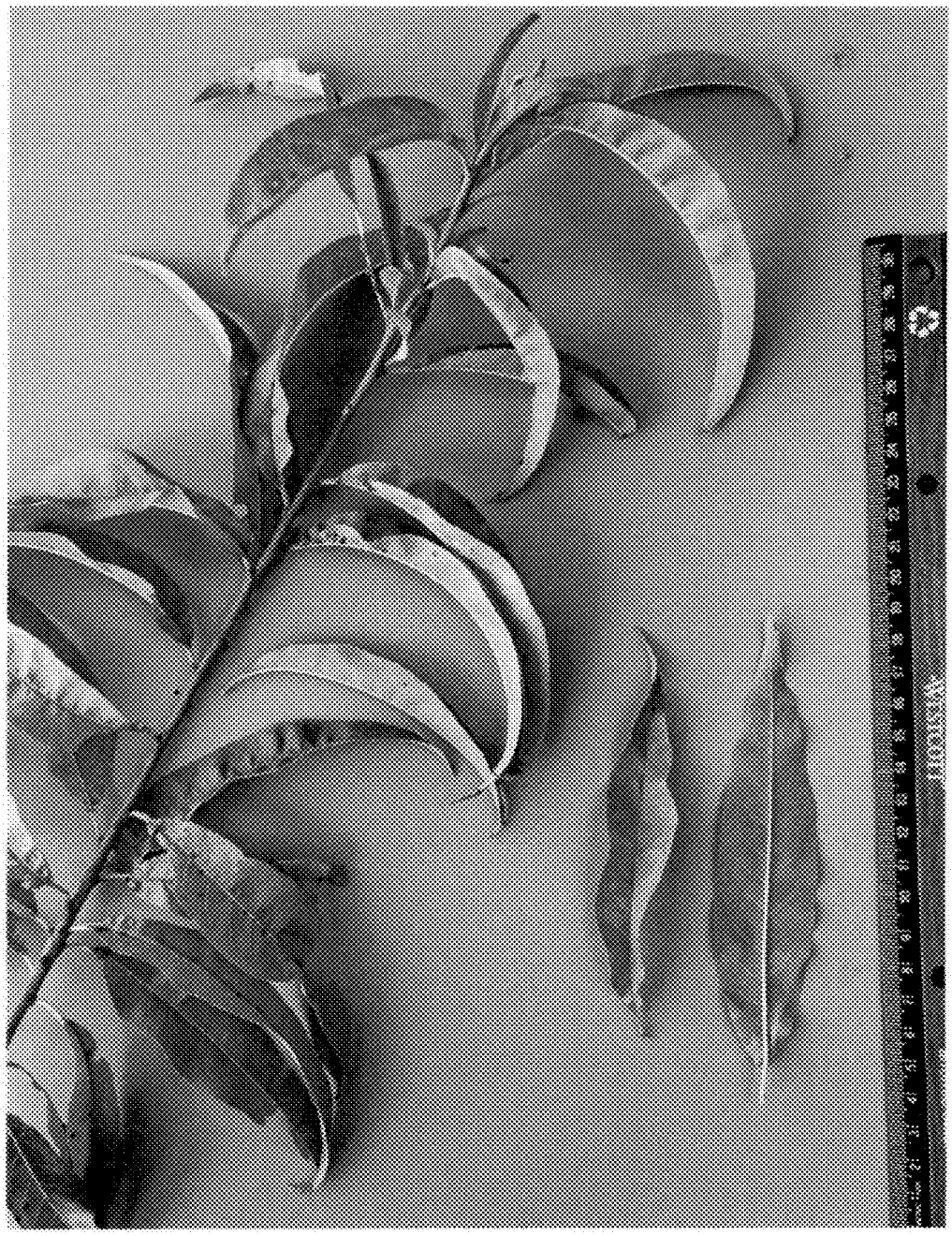
FIG. 4. A stem showing the leaves of 'TRH3E88LW' peach. The ruler is in centimeters.
Figure 5:
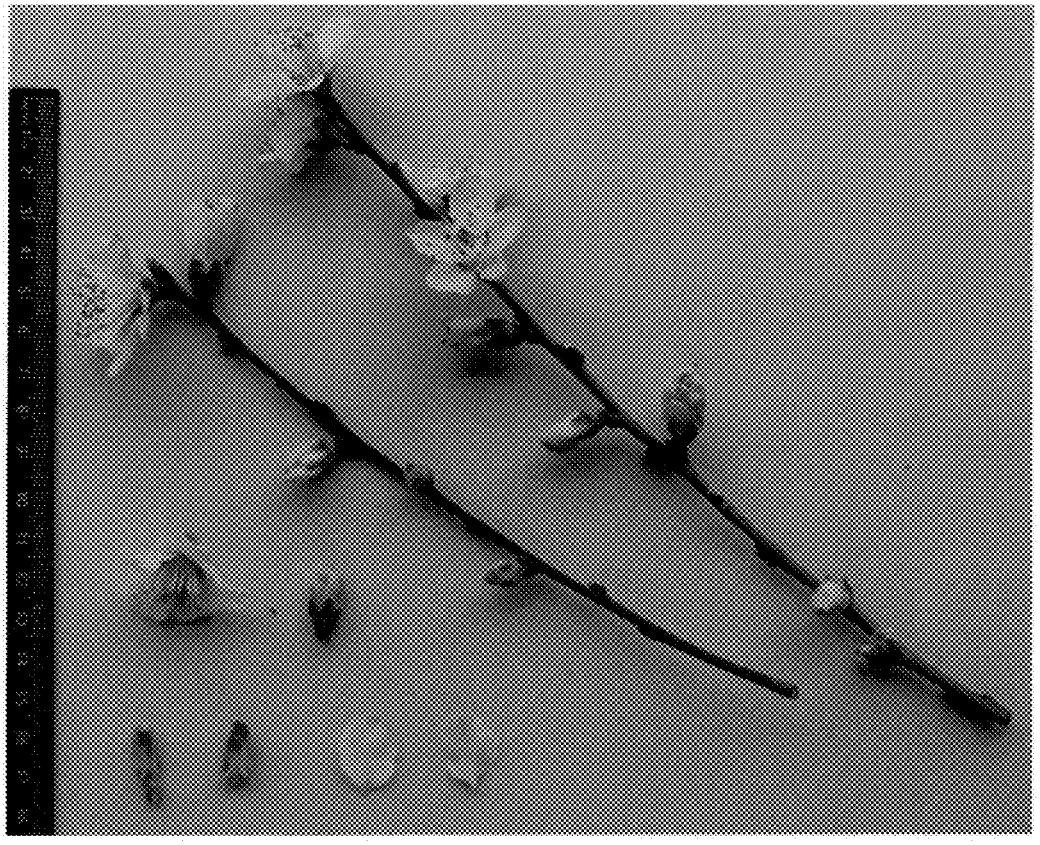
FIG. 5. A stem showing the flowers of 'TRH3E88LW' peach. The ruler is in centimeters.

Referring more specifically to the pomological details of this new and distinct variety of peach tree, the following has been observed under the ecological conditions prevailing at the experimental orchards in the medium chill zone of Texas (Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars grown in the medium chill zone of Texas.

*Height*.—7 feet (2.1 m) at the end of the 2024 growing season.

*Width*.—6 feet width (1.8 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH3E88LW' peach has been trained to an open center configuration but exhibits a semi spreading growth type as seen in peach varieties 'Texprince' (U.S. Plant Pat. No. 14,629) and 'Texking' (U.S. Plant Pat. No. 14,627).

*Current season growth*.—The current season growth for the new variety was approximately 1 to 3 feet (0.3-0.9 m). Vigor is medium compared to other common peach varieties grown in the medium chill zone of Texas.

*Regularity of bearing*.—Regular in the absence of temperatures of 28° F. or below during bloom and considered hardy in the medium chill zone of Texas.

Trunk:

*Size*.—Approximately 2 inches (5 cm) in diameter and 7.5 inches (19 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS2001) present are 156A, 156B, 156C, and 156D of the Greyed-White Group, 157A of the Green-White Group, 166A of the Greyed-Orange Group, 183A and 183B of the Greyed-Purple and 198C and 198D of the Greyed-Green Group.

Branches:

*Size*.—Considered medium for the species.

*Thickness*.—About 3.2 cm in diameter as measured 10 cm from the trunk on a three-year old tree.

*Surface texture*.—Average and appearing furrowed on wood that is several years old.

*Lenticels*.—Numerous flat, oval lenticels present. The lenticels range in size from approximately 4 to 7 mm in width and were approximately 1.5 to 2 mm in height.

*Current season shoots*.—Surface texture-Substantially glabrous.

*Internode length*.—Approximately 10 to 15 mm as measured in the middle of a current season stem.

*Color of mature branches*.—The predominant colors (RHS 2001) are 156D of the Greyed-White Group, 165A, 175A, 175B and 176A of the Greyed-Orange Group and 200D and N200D of the Brown Group.

Leaves:

*Size*.—Considered moderately small to medium for the species. Leaf measurements have been taken from vigorous upright current season growth approximately at mid-shoot.

*Leaf length*.—Approximately 136 to 161 mm.

*Leaf width*.—Approximately 29 to 34 mm.

*Leaf thickness*.—Approximately less than 1 mm.

*Leaf form*.—Lanceolate.

*Leaf tip form*.—Acuminate.

*Leaf upper surface color* (*RHS*2001).—Green, approximately 146A and 146B of the Yellow-Green Group.

*Leaf lower surface color* (*RHS*2001).—Green, approximately 146B and 146C of the Yellow-Green Group.

*Leaf lower mid-vein color* (*RHS*2001).—Light yellow green, 150D of the Yellow-Green Group.

*Leaf margins*.—Form — Considered crenate. Uniformity — Considered generally uniform with occasional waviness.

*Leaf petioles*.—Length — Approximately 8 to 11 mm. Thickness — Approximately 1 to 2 mm. Texture — Glabrous. Color (RHS2001) — Pale green, 150D of the Yellow-Green Group.

*Leaf glands*.—Size — Approximately 1 mm in height and less than 1 mm in width. Number — Generally 2 per leaf. Type — Reniform. Color (RHS2001) — Greenish brown, N199B of the Grey-Brown Group.

*Leaf stipules*.—Length — Approximately 7 to 8 mm. Form — Lanceolate. Color (RHS2001) — Green, 144A, 144B and N144C of the Yellow-Green Group. The stipules are early deciduous. Ratio of wood (leaf) buds to flowering buds-Generally 2 flower buds per vegetative bud.

Flowers:

*Floral buds*.—General — The floral buds are conic in form, and slightly appressed relative to the bearing shoot. Color — Mature buds are brown, (approximately 165A, 166A, 177A of the Greyed-Orange Group, 198A and 198B of the Greyed-Green Group and 200C and 200D of the Brown Group). The buds are considered hardy when grown in the medium chill zone of Texas. Mature Bud Length — Approximately 5 mm. Mature Bud Width — Approximately 1 mm.

*Blooming type*.—Mean date of full bloom in the medium chill zone of Texas was in mid-February (February 22$^{nd}$ at the Somerville and February 16$^{th}$ at the Fairfield experimental plots), with the commercial cultivars 'Texking' (U.S. Plant Pat. No. 14,627) and 'Flordaking' (not patented).

*Flower type*.—Showy.

*Flower size*.—Flower diameter at full bloom is approximately 41 to 45 mm.

*Bloom quantity*.—Considered abundant.

*Flower bud frequency*.—Generally 2 per node.

*Petal size*.—General — Considered medium large to large for the species. Width — Approximately 13 to 15 mm. Length — Approximately 16 to 20 mm.

*Petal form*.—Broadly ovate.

*Petal number*.—Nearly always 5 per flower.

*Petal abaxial/adaxial color* (*RHS*2001).—Medium pink when young (62B, 62C, 62D, 63D, 65B and 65C of the Red-Purple Group), becoming darker near the petal claw.

*Petal claw*.—Form — The claw is considered truncate in shape. Length — Approximately 1 mm. Width — Approximately 1 mm.

*Petal margins*.—Generally considered variable, from nearly smooth to slightly undulate.

*Petal apex*.—Generally-The petal apices appear slightly rounded.

*Flower pedicel*.—Length — Average length of 1 to 2 mm. Thickness — Approximately 1 mm. Color (RHS2001) — A light green (N144D, 145A and 145B of the Yellow-Green Group).

*Floral nectaries*.—Color (RHS2001) — Light to medium orange (15A, 15B, 15C, 16A, 21A, 21B, 23A and 23B of the Yellow-Orange Group and 26A of the Orange Group).

*Sepals*.—Sepal number — Generally five per flower. Surface Texture — The surface has a short, fine, wooly texture. Size — Height 6.9 mm, Width 4.5 mm. Form — Ovate. Color (RHS2001) — Maroon and green with white (approximately 59A, 59B and 60A of the Red-Purple Group; 144B, 144C and N144C of the Yellow-Green Group; 155A, 155B, 155C and 155D of the White Group; 181A and 182A of the Greyed-Red Group and 183A, 183B, 183C, 184A, 185 and 187C of the Greyed-Purple Group).

*Floral cup* (*hypanthium*).—Surface Texture — Generally glabrous. Color (RHS2001) — Maroon with green (approximately 59A, 59B and 60A of the Red-Purple Group; 144B, 144C and N144C of the Yellow-Green Group; 181A and 182A of the Greyed-Red Group and 183A, 183B, 183C, 184A, 185 and 187C of the Greyed-Purple Group).

*Anthers*.—General — Average in size for the species. Color (RHS2001) — Dark red (approximately 34A of the Orange-Red Group and 42A, 42B, 43A, 44A, 45A-, 45, 46A, 46B and 53A of the Red Group).

*Pollen production*.—Pollen is abundant and is a bright yellow color (approximately 1A and 1B of the Green Yellow Group and 2A, 2B, 3A, 3B, 3C, 4A, 4B and 5B of the Yellow Group).

*Filaments*.—Size — Variable in length, approximately 10 to 16 mm, with the filaments being slightly shorter than the pistil height and below the height of the petals. Color (RHS2001) — White (approximately 155A, 155B, 155C, 155D of the White Group) and darkening with advanced maturity.

*Pistil*.—General — Slightly taller than the general anther height and below the petal height. Length — Approximately 16 to 18 mm, including the ovary. Color (RHS2001) — Considered a light yellow-green when young (approximately 1A, 1B, 1C and 1D of the Green-Yellow Group) and becoming slightly darker with advancing senescence.

*Surface texture*.—The variety has a pubescent ovary and style.

Fruit:

*Maturity when described*.—The present variety of fruit is described, as it would be found in its firm ripe condition at full commercial maturity. Under the ecological conditions prevailing in the medium chill zone of Texas it would be ripe in early June. The average ripe date at Pleasanton, Somerville, and Fairfield were June 3$^{rd}$, June 8$^{th}$ and June 7$^{th}$, respectively.

*Size*.—General — Medium large to large for the season and considered uniform. Average Cheek Diameter — Approximately 61 to 65 mm. Average Suture Diameter — Approximately 58 to 60 mm. Average Axial Diameter — Approximately 49 to 51 mm.

*Fruit form*.—Generally considered oblate with unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — The suture is dark red to very dark red. Approximately 46A and 53A of the Red Group, 59A, 59B and 60A of the Red-Purple Group and 185A, 186C, 187A and 187B of the Greyed-Purple Group.

*Ventral surface*.—Form-Considered uniform.

*Stem cavity*.—Width — Approximately 22 to 25 mm. Length — Approximately 22 to 26 mm. Depth — Approximately 9 to 23 mm.

*Fruit base*.—Flat.

*Fruit apex*.—Flat.

*Fruit stem*.—Length — 7 to 9 mm. Thickness — Approximately 3 to 4 mm. Color (RHS2001) — A light to medium green. Varies from 144C, N144D, 145A and 145B of the Yellow-Green Group.

*Fruit skin*.—Generally considered medium or average in thickness. Surface Texture — Light, medium pubescence. Skin Acidity — Considered neutral. Tenacious to Flesh — Yes at commercial maturity. Tendency to Crack — Not observed. Skin Color — Generally-Variable, with approximately 70-90% of the fruit surface covered with a medium to dark reddish pink blush. The fruit skin over color pattern varies from marbled to solid. Blush Color (RHS2001) — Medium to dark reddish pink. 46A and 53A of the Red Group, 59A, 59B and 60A of the Red-Purple Group and N186C, N186D, 187A, 187B and 187C of the Greyed-Purple Group. Skin Ground Color (RHS2001) — Greenish white. Approximately 1D of the Green-Yellow Group, 2D, 4D, 8D, 11C and 11D of the Yellow Group, 155A of the White Group and 158B and 158C of the Yellow-White Group.

*Flesh color* (*RHS*2001).—White with dark pink. Approximately 58A, 59C, 60B and 60C of the Red-Purple Group and 155A. 155B, 155C, and 155D of the White Group. Anthocyanin intensity in the flesh is generally medium next to the skin and weak to medium centrally and next to the stone.

*Flesh fibers*.—Present throughout the flesh.

*Stone cavity color* (*RHS*2001).—White with dark pink. Approximately 58A, 59C, 60B and 60C of the Red-Purple Group, 155A, 155B, 155C, and 155D of the White Group and 158A, 158B, 158C, and 158D of the Yellow-White Group.

*Flesh texture*.—Generally, the flesh is considered firm at commercial maturity.

*Ripening*.—Generally the fruit of the present variety ripens evenly.

*Flavor*.—Considered very sweet (average Brix 13.1) with a rich subacid flavor.

Stone:

*Attachment*.—Semifreestone at commercial maturity.

*Stone size*.—Length — Approximately 27 to 33 mm. Width — Approximately 21 to 23 mm. Thickness — Approximately 16 to 18 mm.

*Fibers*.—Generally a few fibers are attached sporadically along the surface of the stone.

*Stone form*.—Ovate.

*Stone base angle*.—Medium.

*Stone apex angle*.—Medium.

*Stone shape*.—Varies from ovoid to elongated.

*Stone surface*.—Surface Texture — Contains single pits, rosettes of pits and chains of pits. Ridges — Numerous fine ridges are present basally and converge towards the base of the stone.

*Ventral edge*.—Medium.

*Dorsal edge*.—Shape-Grooved and having moderately rough edges.

*Stone color* (*RHS*2001).—The color of the dry stone is light brown with medium to dark pink. Approximately 58A, 59B, 59C, 60B and 61A of the Red-Purple Group, 158A of the Yellow-White Group, 159B of the Orange-White Group, 161D of the Greyed-Yellow, 164D of the Greyed-Orange Group and 186A, 187C and 187D of the Greyed-Purple Group. The color of the inside surface of the endocarp is primarily light brown, 161C and 161D of the Greyed-Yellow Group and 164D and 165D of the Greyed-Orange Group.

*Tendency to split*.—Splitting was not observed.

*Kernel*.—The kernel fills the endocarp at harvest and measures approximately 5 mm in thickness, 8-9 mm in width, and 12-15 mm in length. The colors (RHS2001) of the fresh kernel are light to medium brown, 164B, 164C and 165C of the Greyed-Orange Group.

*Use*.—The subject variety, 'TRH3E88LW', is considered to be a medium chill peach tree of early mid-season maturity, which produces subacid, white-fleshed fruit which are firm with a 70-90% dark reddish pink blush over a greenish-white ground color and are useful for fresh fruit market.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH3E88LW', as illustrated and described herein.

* * * * *